(12) United States Patent
Scharfenberg et al.

(10) Patent No.: US 7,591,340 B2
(45) Date of Patent: Sep. 22, 2009

(54) STEERING AND DRIVING SYSTEM FOR AN INDUSTRIAL TRUCK

(75) Inventors: Stephan Scharfenberg, Tüttleben (DE); Peter Streipardt, Waltershausen (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 477 days.

(21) Appl. No.: 10/588,405

(22) PCT Filed: Jan. 19, 2005

(86) PCT No.: PCT/EP2005/000485

§ 371 (c)(1),
(2), (4) Date: Aug. 3, 2006

(87) PCT Pub. No.: WO2005/077695

PCT Pub. Date: Aug. 25, 2005

(65) Prior Publication Data

US 2008/0314655 A1  Dec. 25, 2008

(30) Foreign Application Priority Data

Feb. 11, 2004  (DE) .................. 10 2004 006 722
May 12, 2004  (DE) .................. 10 2004 023 341

(51) Int. Cl.
*B62D 7/02* (2006.01)
(52) U.S. Cl. .................. 180/252; 180/411; 180/13
(58) Field of Classification Search .................. 180/11, 180/12, 13, 252, 264, 265, 267, 411
See application file for complete search history.

(56) References Cited

U.S. PATENT DOCUMENTS

| 4,513,839 | A | * | 4/1985 | Nieminski et al. .......... 180/253 |
| 4,616,730 | A |   | 10/1986 | Strehler et al. |
| 5,128,598 | A | * | 7/1992 | Avitan .................. 318/587 |
| 5,265,021 | A | * | 11/1993 | Avitan .................. 701/41 |
| 6,032,468 | A |   | 3/2000 | Fetescu et al. |
| 6,145,611 | A | * | 11/2000 | Haddad, Sr. .................. 180/12 |
| 6,367,571 | B1 | * | 4/2002 | Schwarz .................. 180/253 |
| 6,491,127 | B1 | * | 12/2002 | Holmberg et al. .......... 180/252 |
| 2008/0004148 | A1 | * | 1/2008 | Rogg .................. 475/169 |

FOREIGN PATENT DOCUMENTS

| DE | 34 20 146 A1 | 12/1985 |
| DE | 41 10 792 A1 | 10/1992 |
| DE | 691 09 453 T | 9/1995 |
| DE | 197 20 789 A1 | 11/1998 |
| DE | 199 04 552 A1 | 9/1999 |
| DE | 199 49 351 A1 | 7/2001 |
| DE | 101 30 100 A1 | 1/2003 |
| EP | 0 507 137 A1 | 10/1992 |

* cited by examiner

*Primary Examiner*—Kevin Hurley
(74) *Attorney, Agent, or Firm*—Davis & Bujold, P.L.L.C.

(57) ABSTRACT

A steering and driving system (1, 53, 54) for an industrial truck with a driving engine (2), a driving transmission (21), a steering engine (4) and a steering transmission (5, 32, 32'), through that one rotor (23) arranged on a wheel hub (22) could be driven and is swivelable at a vertical axis (V). For the realization of the compact design form as well as lesser manufacturing costs for this steering and driving system is considered, that the driving engine (2), the steering engine (4) and the steering transmission (5, 32, 32') are arranged co-axially to each other.

19 Claims, 2 Drawing Sheets

STEERING AND DRIVING SYSTEM FOR AN INDUSTRIAL TRUCK

This application is a national stage completion of PCT/EP2005/000485 filed Jan. 19, 2005 which claims priority from German Application Serial No. 10 2004 006 722.8 filed Feb. 11, 2004 and German Application Serial No. 10 2004 023 341.1 filed May 12, 2004.

FIELD OF THE INVENTION

The invention concerns the steering and drive wheel for an industrial truck.

BACKGROUND OF THE INVENTION

A controllable drive wheel for an industrial truck with two drive gears is known from the DE 41 10 792 C2. A miter gear with two miter wheel gears is arranged such that a respective output spindle drives the drive gears. The miter gear is driven by an electrical drive motor on a planetary gear that is arranged parallel or co-axial to the central axis of the device. Furthermore, a steer wheel motor is provided and is mounted outside the wheel gear case directly on the chassis of the industrial truck or on an additionally arranged head, plate torque proof to the chassis. With the operation of this steer wheel motor, this turns on a steer gear stage the wheel gear case or the gear carrier in its rotating assembly journal and thus also the wheel gear with both the wheel drives at the steering axle. The disadvantage of this steerable wheel drive is that the lateral arrangement of at least the steer drive motor makes the entire device less compact.

In addition, DE 199 04 552 A1 shows a wheel drive for an industrial truck for which an electrical traction motor and a gear driven by this are arranged co-axial to the longitudinal axis of the hub of the wheel of rotor. The traction motor is thereby designed as an electric motor with a disc-shaped rotor. Furthermore, the wheel drive exhibits electromotor steering with a steer motor and a steer gear, by which the steer motor is necessarily arranged perpendicular to the stage and is mounted by the turning of the rotor by the entire longitudinal axle of the wheel hub, traction motor and gear. The steer gear is a Wolfram-gear.

Although this wheel drive is very compact in the entire device, through the mentioned wheel hub drive as well as integration of the steer motor and the steer gear, its constructive formation, especially due to the cramped measure in the area of the wheel hub is comparatively complex and, therefore, costly. A further disadvantage is considered that the revealed combination of traction motor and gear, as well as steer motor and steer gear, develops a relatively large diameter size wheel drive.

Against this background, the task underlying the invention is to manage a constructively simple electro-motor steering and driving system for an industrial truck that exhibits a small diameter compared to known steering and driving systems and which could be manufactured at a comparatively cheaper cost with an acceptable design.

SUMMARY OF THE INVENTION

The invention concerns a steering and driving for an industrial truck with a driving engine, a traction motor, a steering engine and a steering transmission, through which at least a rotor arranged on a wheel hub of an industrial truck is drivable and is rotatable at a vertical axis. It is important with this steering and driving system that the traction motor, steering engine and the steering transmission are arranged co-axial to each other. Thereby, with an acceptable installation height, an especially radial compact design results as well as through the increased integration grade, for example, the double usage of housing components, at a comparatively lower manufacturing cost.

An especially preferred embodiment of the invention thereby provides that the driving engine, the steering engine and the steering transmission are arranged axially in this sequence, one after another, while the driving transmission, formed as a miter gear, is linked with a rotating assembly driven by a steering engine on the steering transmission and is arranged axially behind the steering transmission.

In a further constructive training of the specified design principle, it is considered that the driving engine is formed as a solid shaft and the steering engine shaft as a hollow shaft, as well as that the traction motor is led co-axially through the steering motor shaft.

Furthermore, it is considered that the traction motor carries a spur-wheel on its further end from the traction motor, which is there in tooth engagement with a spur-wheel on the input shaft of the traction gear, formed as a miter gear. The output shaft of this motor gear is linked with a wheel hub of at least a rotor.

In a further design of the invention, the steering transmission is designed as a multi-leveled planetary gears and/or a Wolfram-gear, whereby the latter exhibits an advantage due to its axially shorter length with higher gear reduction.

Furthermore, the invention concerns the drive-technical link between the steering engine and the steering transmission, as well as between the steering transmission and the swivel drive of the driving transmission or of a rotor at least linked with the latter. In this context, it is considered that the steering engine shaft is designed as the first sun wheel, whose external tooth system is in tooth engagement with the teeth of planetary wheels of the steering transmissions.

With the usage of multi-leveled planetary gears as steering transmission, it is preferably considered that the planetary wheels of the first planetary wheel are level with the first mentioned sun wheel and are stored on a first planetary carrier, which is linked slip free with a second sun wheel. On this second planetary carrier, rotary stored planetary wheels of the second planet wheel stage are meshed with the external tooth system of the second sun wheels, whereby the planet wheels of the first and the second planet wheel level are located in tooth engagement with a fixed hollow wheel or two fixed hollow wheels. Additionally, it is considered that the second planetary carrier is linked slip free with a third sun wheel, that the third sun wheel is in tooth engagement with planet wheels of the third planet wheel stage, that the planet wheels of the third planet wheel stage are stored rotating on a third planetary carrier, which is linked slip free with the hollow wheel and that the planet wheels of the third planet wheel set is in tooth engagement with an internal tooth system of the journal internal ring of rotary assembly journal, which is linked slip free with the rotary assembly or directly with the housing of the traction gear.

Another detail of the invention is thereby indicated that the journal external ring of rotary assembly journal is slip free linked with a vehicle framework of an industrial truck.

It could be further considered that the housing of the steering engine is held on with the fastener axially on the journal outer ring. Further, the compact design of this steering and driving system thereby prefers that the specified hollow wheel and the radial external end of third planetary carrier are arranged between the external wall of the steering engine housing and the journal external ring, behind each other. In this manner, the steering engine housing can be fixed against the journal external ring of rotary assembly by the mentioned fastener that are simultaneously linked as a hollow wheel affecting as a steering transmission housing as well as the third planetary carrier axially with each other.

In addition, it can be planned in a deviation that the steering transmission housing is fixed slip free on the separate fastener on the journal external ring of rotary assembly.

A preferred variation of the invention is thereby given, that a brake is arranged affecting the driving engine shaft on the driving transmission's farther end of the steering and driving system. This brake is preferably designed as electrically activated, while it is considered possible regarding the steering engine to design this as an electric motor with a disc-shaped rotor.

Further, it could be considered that the housing of the driving engine is fixed on the housing of the driving engine or an entire housing is used by both the engine elements. This housing and/or the single housing is designed as a sheet construction.

Additionally, it is profitably assessed if the steering transmission housing, the journal external ring of rotary assembly or the rotary assembly exhibits a bore for recording by swiveling angle sensors; with its help the swiveling of the rotor is ascertainable at its steering axle and is communicated to a control device.

Regarding the recording of the steering angle for usage in a control device allocated to the steering and driving system, it can be considered on the rotor of the steering engine, on the fixed journal outer ring of the rotary assembly and/or on the rotary assembly signal indicator as a magnet, which interacts together with the specified swiveling angle sensors for swiveling angle detection.

As per another aspect of the invention, it is considered that a flange, pointing radially outward, especially a ring flange, is formed on the steering transmission housing as well as on the steering engine housing, respectively, through which respective axial bores, fixing screws are fed for fixing the same on the journal external ring.

Such an example, with one or all of the specified features of highly integrated steering and driving system, as a further advantage, exhibits reduced noise pressure, especially at the time of changing the pressure, and has low maintenance and/or is maintenance free, because the steering transmission could be filled with a lifetime lubricant, and also the steering engine can be of a maintenance free design by using a brushless dc motor or alternating current motor in standard or shrunk-on-disc design.

For the reduction of manufacturing costs, it is further advised to design the planetary carrier as a sheet construction with an open or closed design.

BRIEF DESCRIPTION OF THE DRAWINGS

The invention will now be described, by way of example, with reference to the accompanying drawings in which.

DETAILED DESCRIPTION OF THE INVENTION

Figure 1:
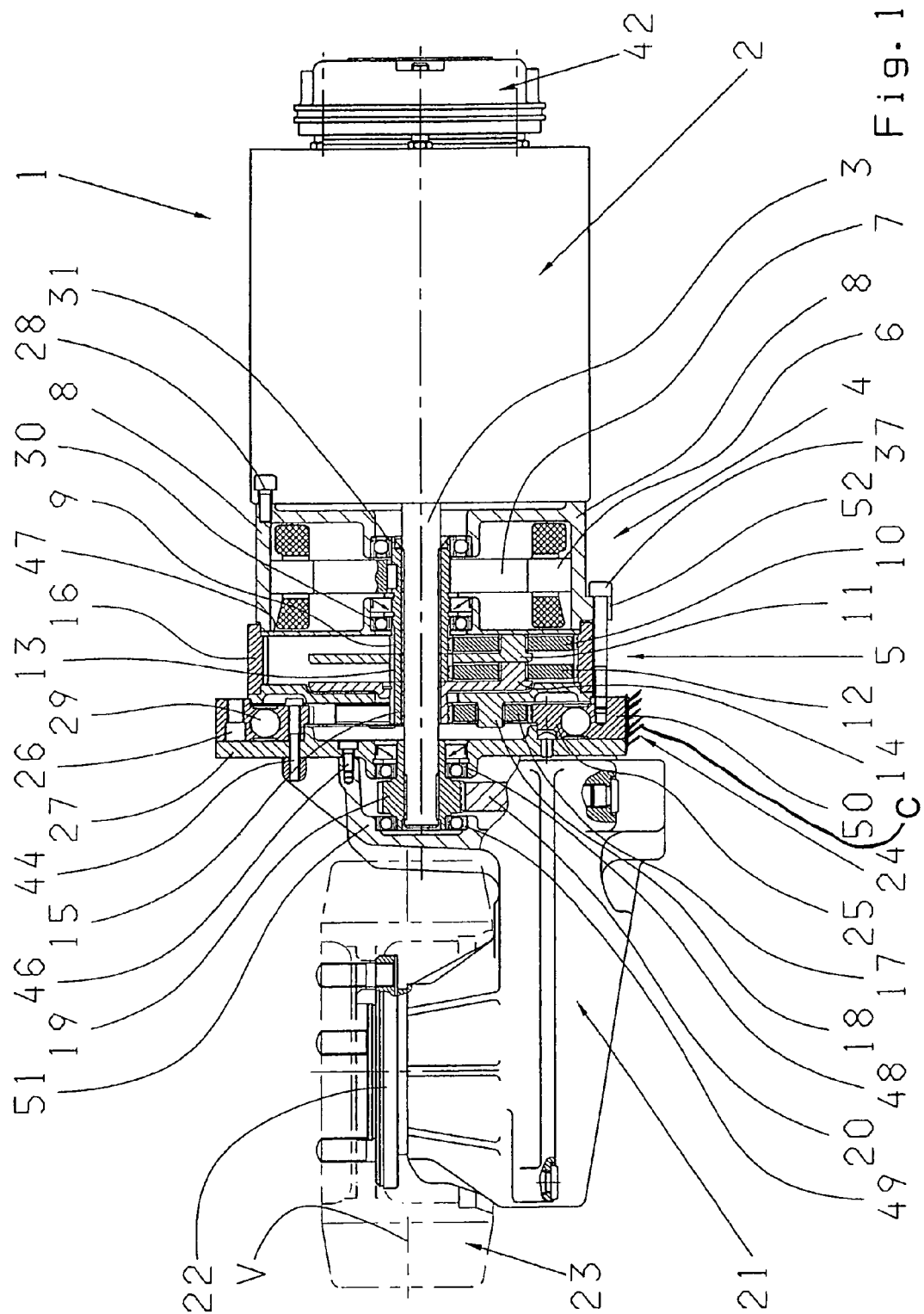
FIG. 1 is a partial section represented with a lateral view of an electromotor steering and driving system for an industrial truck.

According to FIG. 1, a steering and driving system 1 designed according to the invention, as the main component, an industrial truck (of vehicle) initially has a driving engine (traction motor) 2, by which a driving shaft (traction motor shaft) 3 is driven on a driving transmission (traction gear) 21 of a rotor 23. The rotor 23 is rotatable, together with the driving transmission 21, along a vertical axis V. For the execution of this swivel movement, the steering and driving system 1 allotted on an electric steering engine (steering motor) 4, on which a steering transmission (steering gear) 5 is arranged. For gear reduction of the steer motor revolution, the output of this steering transmission gear 5 affects a rotary assembly 27 that is linked slip free with a housing 51 of driving transmission 21. Particularly, it is of importance for the steering and driving system 1 designed according to the invention that the driving engine 2, the steering engine 4 and the steering transmission 5 are arranged co-axial with each other.

In detail, this steering and driving system 1 is designed in such a manner that the driving engine shaft 3 is a solid shaft and is fed through a hollow shaft placed by a steering engine shaft (steering motor shaft) 9. A first spur-wheel 19 is fixed on the driving engine shaft 3 on the far end its traction motor, which meshes with a second spur-wheel 20 that is on a gearbox input shaft of the driving transmission (traction gear) 21 (not shown here). In this traction gear, the drive torque is managed in the known manner on an angle drive to a gear output shaft that is linked slip free with a wheel hub 22. The rotor 23 is fixed on this wheel hub 22 with screws.

Further, a brake 42 is fixed on the traction motor housing above driving engine 2 co-axial to the vertical axis V which affects the driving engine shaft 3 if required and is particularly activated with elasticity and is electrically ventilated.

The steering engine 4 is designed here as a shrunk-on-disk rotor and is available on a stator 6 and a rotor 7, which are placed in a steering engine housing 8, 8'. Thereby the stator 6 is linked on a fixing element which not indicated further with the steering engine housing 8, 8', while the rotor 7 is fixed on the already-mentioned steering engine shaft 9.

As represented in FIG. 1 on left of vertical axis V, the gear housing of the driving engine 2 can be fixed on the steering engine housing 8 by way of fixation screws 28, while the right figure half could be extracted from the deviating design, for which the steering engine 4 and the driving engine 2 display a total housing 8'.

Further, FIG. 1 shows that the driving engine far side of steering engine 4 is covered by a cap 47, which is clamped axially between the housing 8, 8' of steering engine 2 and a hollow wheel 16 serving as a housing element.

The steering engine shaft 9 is on a roller bearing 30, 31 on which the cap 47, serving as a bearing shield, and on the housing 8,8' of steering and driving is supported revolving as well as packed on seal. It serves in a technical multi-level planetary steering transmission 5 as first sun wheel on the steering engine 4 drive. The outer teeth of this first sun wheel 9 meshes thereby with the teeth of planet wheels 10 of the first planetary wheel stage that are supported revolving on a first planetary carrier 11. This first planetary carrier 11 is linked slip free with a second sun wheel 13 which axially connects to the spur wheel 19 on the first sun wheel 9 (steering engine shaft 9).

The outer teeth of the second sun wheel 13 are engaged with teeth of the planet wheels 12 of the second planet stage, which is supported revolving on a second planetary carrier 14. Thereby the planet wheels 10, 12 of the first and the second planet wheel stage is engaged with the fixed hollow wheel 16.

The second planetary carrier 14 is linked slip free with a third sun wheel 15 which meshes with planet wheels 17 of the third planet wheel stage. This planet wheel 17 of the third planet wheel stage is revolving supported on a third planetary carrier 18, which is linked slip free with the mentioned hollow wheel 16.

Eventually the planetary carrier 18 of the third planet wheel set stands effectively engaged with the inner teeth of a bearing inner ring 25 of a rotary assembly 24, which is linked slip free on a fixation screw 44 with the rotary assembly 27. An outer ring 50 as well as a rolling element 29, enclosed between the rings 25, 50 belong to the rotary assembly 24.

Further, it is seen in FIG. 1 that preferably the traction gear housing 51 is linked slip free by fixation screws 46 with the rotary assembly 27. Furthermore, this representation clarifies that the driving engine shaft 3 is supported above the spur-wheel 19 on a roller bearing 48 with the rotary assembly 24 and below the same on a roller bearing 49 in the traction gear housing 51.

The outer ring 50 of the rotary assembly 24 is firmly combinable with the chassis C of the industrial truck whereby in this outer ring 50, a bore 26 is designed with a screw thread, in which a fixation screw is screwed in, meshing these two parts.

Finally, FIG. 1 shows that on housing 8 of steering engine 4, an outward radial flange 52, that can be built from one or more plates, is arranged, fastened by a fixation screw 37 led through its axial bore. The thread section of the fixation screw 37 is screwed in a thread in the outer ring 50 of rotary assembly 24, 50 that the housing 8' of steering engine is ascertained with the hollow wheel 16 serving as housing section and the third planetary carrier 18 as well as the cap 47 axial against the bearing outer ring 50 and thus against the chassis C of the industrial truck.

Figure 2:
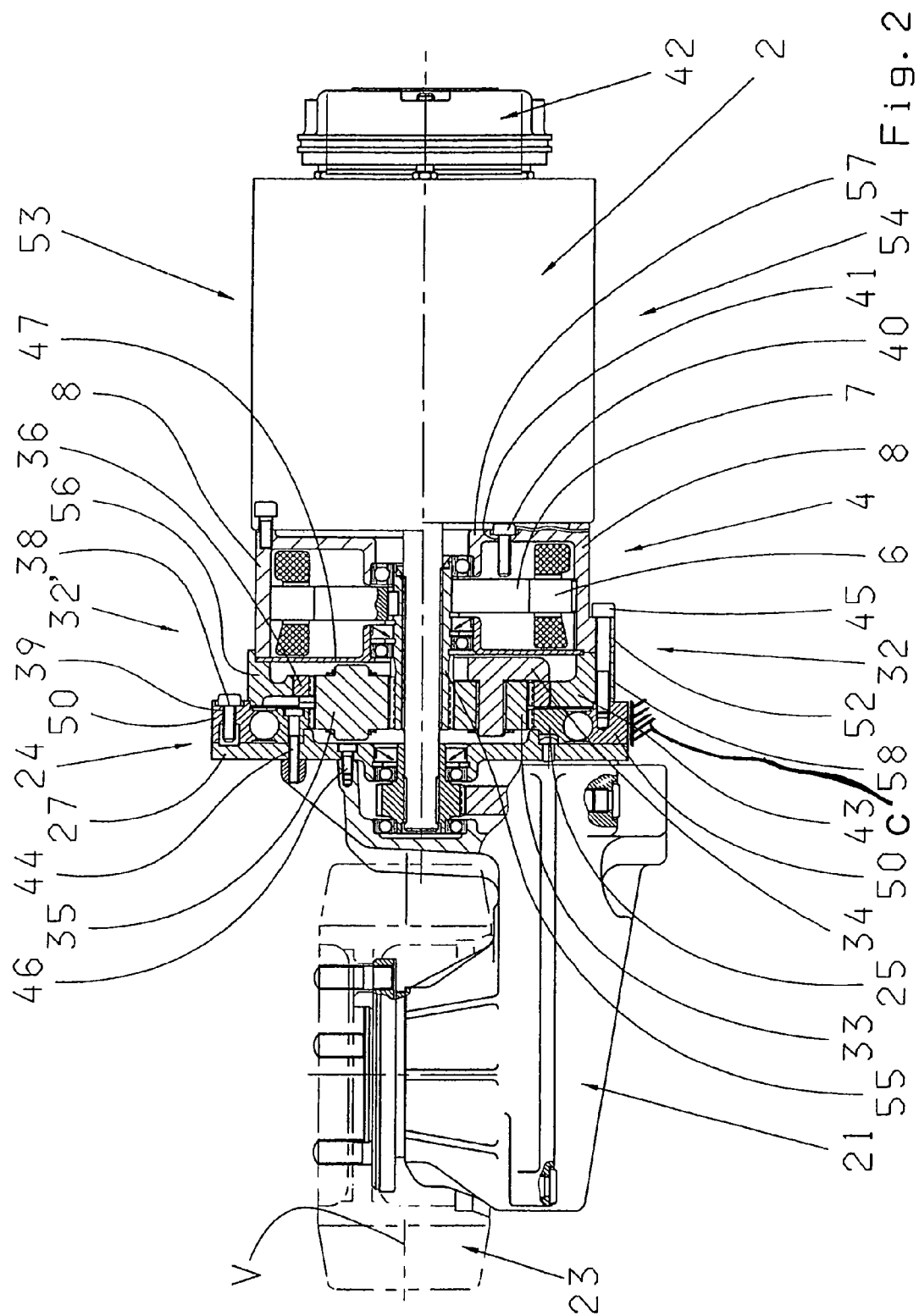
FIG. 2 is a representation as in FIG. 1, however related to a second design example of the invention.

The design represented in FIG. 2 of two further variations of the invention formed steering and driving system 53, 54 differs from the steering and driving system 1, represented in FIG. 1, in that the steering transmission is designed as a Wolfram-gear 32, 32' and not as a multi-level planet gear.

Also for both these design forms the steering engine shaft (steering motor shaft) 55 serves as sun wheel and carries an outer gearing which is engaged with the teeth of planet wheels 33 and/or 35. For the second design variations, right near the vertical axis V, the planet wheels 33 are supported slip free on a planetary carrier 34 and are additionally engaged with an inner gearing on an inward radial section of a steering transmission housing 43. Further, the planetary carrier 34 meshes with the inner gearing of inner ring 25 of the rotary assembly 24 already known from FIG. 1, so that the rotary assembly 27 is rotatable at the vertical axis V by the steering engine 4.

A hollow wheel 36 is thereby fixed or integrated with it on the radial inward projecting section of the steering transmission housing 43, which is ascertained by way of fixation screws 45 on the outer ring 50 of the rotary assembly 24.

As shown in FIG. 2 to the right of the vertical axis V, it is preferable if the fixation screws 45 penetrate the flange 52 of steering engine housing 8 as well as also a bore in flange 58 on steering transmission housing 43 so that, in this manner, both the upper engine elements 2, 4 are centered to the steering transmission housing 43 and are ascertained against the bearing outer ring 50 of the rotary assembly 24.

At the left of the vertical axis V, a third variation represents the planet wheels 35 of Wolfram-steer transmission 32' display geometry as the aforementioned planet wheels 33. Thereby it is especially striking that this exhibits the designed rotating axis on the planet wheels 33 and not the bore for recording of rotating axis of planet wheels 33. This intervenes in the recording opening of visible planetary carrier.

In addition, in FIG. 2 it can be seen that the axial short forming steering transmission 32' exhibits the hollow wheel 36, with which the planet wheel 35 is engaged. This hollow wheel 36 is linked slip free or integrated with an inward radial section of steering transmission housing 43. The steering transmission housing 43 is clamped on the sides under the interlayer of the cap and/or the bearing shield 47 of steering engine 4 between its housing 8 and the outer ring 50 of rotary assembly 24.

Finally, FIG. 2 shows that in the steering and driving system 32, 32', sensors 38, 40 can be installed with which the rotation of rotary assembly 27 is identifiable against the lying drive elements.

In the case of the second variation of the steering and driving system 32, this angle of rotation 40 is inserted in a recording opening 41 of an inward radial and section 57 serving as a bearing shield of combined housing 8' by the driving and steering engines and measures the named swivel movement on the rotor 7 of the steering engine 4.

For the third variation of the steering and driving system 32' (left near the vertical axis V represented), the sensor 38 is inserted in a recording opening 39 in the outer ring 50 of rotary assembly 24. In this case, the swivel between the outer ring 50 and the rotary assembly 27 is ascertained and informed to a control device (not shown here).

REFERENCE NUMERALS

1 steering and driving system
2 driving engine
3 driving engine shaft
4 steering engine
5 steering transmission
6 stator steer motor
7 rotor steer motor
8 steering engine housing
9 steering engine shaft; first sun wheel
10 planet wheel of first planet wheel stage
11 first planetary carrier
12 planet wheel of second planet wheel stage
13 second sun wheel
14 second planetary carrier
15 third sun wheel
16 hollow wheel
17 planet wheel of third planet wheel stage
18 third planetary carrier
19 spur-wheel
20 spur-wheel
21 driving transmission
22 wheel hub
23 rotor
24 rotary assembly
25 bearing inner ring with inner wheel teeth
26 bore
27 rotary assembly
28 fixation screw
29 rolling element
30 roller bearing
31 roller bearing
32 Wolfram-steer transmission (variation 2)
32' Wolfram-steer transmission (variation 3)
33 planet wheel of Wolfram-steer transmission (variation 2)
34 planet carrier of Wolfram-steer transmission
35 planet wheel of Wolfram-steer transmission (variation 3)
36 hollow wheel of Wolfram-steer transmission
37 fixation screw
38 angle of rotation sensor
39 recording opening in outer ring of rotary assembly bearing
40 angle of rotation sensor 41 recording opening in housing section 57
42 brake
43 housing Wolfram-gear (variation 2)
44 fixation screw
45 fixation screw
46 fixation screw
47 cap of steer gear
48 roller bearing
49 roller bearing
50 outer ring of rotary assembly
51 housing of traction gear
52 flange on housing 8
53 steering and driving system
54 steering and driving system
55 steering engine motor shaft for Wolfram-gear
57 housing section on housing 8'
58 plate or flange on steering transmission housing 43
V vertical axis

The invention claimed is:

1. A steering and wheel drive (1, 53, 54) for a ground conveyor having:
   a traction motor (2),
   a traction gear (21),
   a steering motor (4), and
   a steering gear (5, 32, 32'),
   wherein a rotor (23), arranged on a wheel hub (22) is driven and swivels about a vertical axis (V), the traction motor (2), the steering motor (4) and the steering gear (5, 32, 32') are arranged coaxially with each other, the traction motor (2) drives the fraction gear (21) via first and second spur-wheels (19, 20), and the steering motor (4) is located adjacent the traction motor (2); and
   a traction motor shaft (3), driven by the traction motor (2), is a solid shaft and a steering motor shaft (9, 55), driven by the steering motor (4), is a hollow shaft.

2. The steering and wheel drive according to claim 1, wherein the steering motor (4) is located between the traction motor (2) and the steering gear (5, 32, 32').

3. The steering and wheel drive according to claim 1, wherein the traction motor shaft (3) is co-axial with and surrounded by the steering motor shaft (9, 55).

4. The steering and wheel drive according to claim 1, wherein the first spur-wheel (19) is located on an opposite end of the traction motor shaft (3), remote from the traction motor (2), and the first spur wheel (19) of the traction motor shaft (3) engages with the second spur-wheel (20) which forms part of the traction gear (21).

5. The steering and wheel drive according to claim 4, wherein the second spur-wheel (20) is fixed on the input shaft of the fraction gear (21) and the traction gear (21) is coupled with a hub wheel (22) of the rotor (23).

6. The steering and wheel drive according to claim 1, wherein a brake (42) is arranged on an end of the fraction motor (2), remote from the first spur-wheel (19) supported by the fraction motor shaft (3), for braking rotation of the traction motor shaft (3).

7. A steering and wheel drive (1, 53, 54) for a ground conveyor having:
   a traction motor (2);
   a traction gear (21);
   a steering motor (4); and
   a steering gear (5, 32, 32');
   wherein a rotor (23), arranged on a wheel hub (22) is driven and swivels about a vertical axis (V), the traction motor (2), the steering motor (4) and the steering gear (5, 32, 32') are arranged coaxially with one another, the traction motor (2) drives the traction gear (21) via first and second spur-wheels (19, 20), and the steering motor (4) is located adjacent the traction motor (2); and
   the steering gear (5) is at least one of a multi-level planet gear and a Wolfram-gear (32, 32').

8. The steering and wheel drive according to claim 7, wherein a steering motor shaft has a first sun wheel (9, 55) which has an outer gearing engaging with teeth of a first planet carrier (10, 33, 35) of the steering gear (5, 32, 32').

9. The steering-and wheel drive according to claim 7, wherein planet wheels (10) of a first planet wheel stage mesh with a first sun wheel (9) and are rotatably supported on a first planet carrier (11), which is linked slip free with a second sun wheel (13), a second planet carrier (14) meshes with an outer ring gearing of a second sun wheel (13) which meshes with a second planet carrier (12), the first and the second planet carriers (11, 12) of the first and the second planet wheel stages mesh with a fixed hollow wheel (16), the second planet carrier (14) is linked slip free with a third sun wheel (15), the third sun wheel (15) meshes with a planet carrier (17) of a third planet wheel stage, the planet wheels (17) of the third planet wheel stage are rotatably supported on a third planet carrier (18) which is linked slip free with the hollow wheel (16), the planet wheels (17) of the third planet wheel stage mesh with an inner gearing of an inner bearing ring (25) of a rotary assembly (24), which is one of linked slip free with one of a rotary assembly (27) and directly with a housing (51) of the fraction gear (21).

10. The steering and wheel drive according to claim 9, wherein an outer bearing ring (50) of the rotary assembly (24) is linked slip free with a chassis (C) of an industrial vehicle.

11. The steering and wheel drive according to claim 9, wherein a housing (8, 8') of the steering motor (4) is fixed to the outer bearing ring (50) by a fastener (37).

12. The steering and wheel drive according to claim 9, wherein the hollow wheel (16) and a radial external end of the third planet carrier (18) are arranged between an outer wall of a steering motor housing (8, 8') and the outer bearing ring (50).

13. The steering-and wheel drive according to claim 9, wherein a steering gear housing (16) is slip free linked with the outer bearing ring (50) of the rotary assembly bearing (24).

14. The steering-wheel drive according to claim 9, wherein the outer bearing ring (50) of one of the rotary assembly bearing (24) and the rotary assembly (27) has an opening (39) which accommodates a ring sensor (38) for sensing an angle of rotation of the outer ring 50.

15. The steering and wheel drive according to claim 9, wherein an indicator is placed on at least one of:
   a rotor (7) of the steering motor (4),
   the outer bearing ring (50) of the rotary assembly bearing (24), and
   the rotary assembly (27)
for identifying an angle of rotation of the steering and wheel drive.

16. The steering-and wheel drive according to claim 9, wherein at least one of:
   an outward radial flange (52) of the steering motor housing (8, 8'), and
   a plate (58)
of a housing (43) of the steering gear (32, 32') is fixed to the outer bearing ring (50) by fixation screws (37, 45).

17. A steering and wheel drive (1, 53, 54) for a ground conveyor having:
- a fraction motor (2);
- a traction gear (21);
- a steering motor (4); and
- a steering gear (5, 32, 32');
- wherein a rotor (23), arranged on a wheel hub (22) is driven and swivels about a vertical axis (V), the traction motor (2), the steering motor (4) and the steering gear (5, 32, 32') are arranged coaxially with one another, the traction motor (2) drives the traction gear (21) via first and second spur-wheels (19, 20), and the steering motor (4) is located adjacent the traction motor (2); and
- the steering motor (4) is an electric motor with a disc-shaped rotor.

18. The steering and wheel drive according to claim 17, wherein one of:
- a housing of the traction motor (2) is fixed to a housing (8) of the steering motor (4), and
- the traction motor (2) and the steering motor (4) are both accommodated by a combined housing (8').

19. A steering and wheel drive (1, 53, 54) for a ground conveyor having:
- a traction motor (2);
- a traction gear (21);
- a steering motor (4); and
- a steering gear (5, 32, 32');
- wherein a rotor (23), arranged on a wheel hub (22) is driven and swivels about a vertical axis (V), the traction motor (2), the steering motor (4) and the steering gear (5, 32, 32') are arranged coaxially with one another, the traction motor (2) drives the traction gear (21) via first and second spur-wheels (19, 20), and the steering motor (4) is located adjacent the traction motor (2); and
- a steering motor housing (8') has an opening (41) which accommodates a rotor sensor (40) for sensing an angle of rotation of a rotor (7) of the steering motor (4).

* * * * *